(12) United States Patent
Palmer (10) Patent No.: US 8,088,956 B2
(45) Date of Patent: Jan. 3, 2012

(54) BPA PROCESS IMPROVEMENT

(75) Inventor: David P. Palmer, Katy, TX (US)

(73) Assignee: Stone & Webster, Inc, Houston, TX (US)

( * ) Notice: Subject to any disclaimer, the term of this patent is extended or adjusted under 35 U.S.C. 154(b) by 0 days.

(21) Appl. No.: 13/006,547

(22) Filed: Jan. 14, 2011

(65) Prior Publication Data

US 2011/0112333 A1    May 12, 2011

(51) Int. Cl.
*C07C 37/68* (2006.01)

(52) U.S. Cl. .......................... 568/749; 568/758; 568/759

(58) Field of Classification Search .................. None
See application file for complete search history.

(56) References Cited

U.S. PATENT DOCUMENTS

| | | | |
|---|---|---|---|
| 3,963,610 A | 6/1976 | Hauschulz et al. | |
| 4,262,150 A * | 4/1981 | Pujado | 568/754 |
| 4,469,561 A | 9/1984 | Sikdar et al. | |
| 4,950,805 A | 8/1990 | Iimuro et al. | |
| 4,973,766 A * | 11/1990 | Penzo et al. | 568/754 |
| 5,344,528 A | 9/1994 | Bossler et al. | |
| 5,345,000 A | 9/1994 | Moriya et al. | |
| 6,071,409 A | 6/2000 | Bondy et al. | |
| 6,806,394 B2 | 10/2004 | Evitt et al. | |
| 6,824,687 B2 | 11/2004 | Panditrao et al. | |
| 6,972,345 B2 | 12/2005 | Blaschke et al. | |

FOREIGN PATENT DOCUMENTS

| | | |
|---|---|---|
| EP | 0758636 | 1/2000 |
| WO | 00/35847 | 6/2000 |
| WO | 2007/044139 | 4/2007 |

OTHER PUBLICATIONS

Narasimhan et al., Solubility and Equilibrum Data of Phenol-Water-n-Butyl Acetate System at 30° C., Journal of Chem. and Eng. Data., 7 (3) p. 340 (1962).
Narasimhan et al., Solubility and Equilibrum Data of Phenol-Water-Isoamyl Acetate and Phenol-Water-Methyl Isobutyl Ketone Systems at 30° C., Journal of Chem. and Eng. Data., 7 (4) p. 457 (1962).

* cited by examiner

*Primary Examiner* — Brian J Davis
(74) *Attorney, Agent, or Firm* — Roberts Mlotkowski Safran & Cole, P.C.

(57) ABSTRACT

The present disclosure enables phenol recovery, purification and recycle in a simple, economic manner from waste streams from, for example, a phenol/acetone production process, e.g., a phenol/acetone plant or an upstream cumene hydroperoxide cleavage process step, and BPA production step, for use in the reaction with acetone to produce BPA. The disclosure therefore reduces the overall consumption of phenol in the production of BPA.

8 Claims, 2 Drawing Sheets

BPA PROCESS IMPROVEMENT

CROSS REFERENCE TO RELATED APPLICATIONS

This application claims the benefit of application Ser. No. 12/113,332, filed May 1, 2008, now U.S. Pat. No. 7,902,408, the disclosure of which is incorporated by reference in its entirety.

FIELD OF THE INVENTION

The present disclosure relates to an improved process for producing bisphenol-A (BPA). BPA is a commercially significant compound used to manufacture polycarbonates, other engineering thermoplastics and epoxy resins. The polycarbonate application in particular demands high purity BPA due to stringent requirements for optical clarity and color in the finished application. Accordingly, those skilled in the art continually strive to improve the product quality of BPA in more economically efficient process schemes. The present disclosure concerns a more economical process scheme to produce high purity BPA in improved yield.

BACKGROUND OF THE INVENTION

BPA and its manufacture is described U.S. Pat. No. 4,950,805 (Iimuro et al.); U.S. Pat. No. 5,345,000 (Moriya et al.); and U.S. Pat. No. 6,806,394 (Evitt et al.), which patents are incorporated herein by reference.

BPA is produced commercially by the condensation of acetone and phenol over an acid catalyst and, in fact, BPA production is the largest consumer of phenol. Currently, the most common route for the production of phenol comprises a four-step process in which the first step involves alkylation of benzene with propylene to produce cumene, followed by oxidation of the cumene to the corresponding hydroperoxide, followed by cleavage of the hydroperoxide to produce equimolar amounts of phenol and acetone, as well as other reaction byproducts, and then a series of steps to separate and purify acetone and phenol from each other and from unwanted reaction byproducts which produces a waste stream comprising water, unrecovered phenol, unrecovered acetone, and other reaction byproducts.

The production of BPA consumes two moles of phenol and one mole of acetone to produce one mole of BPA and one mole of water. In subsequent process steps, the water is removed from the process and the BPA is purified. According to the present disclosure, an integrated process in which part of the required phenol is produced from cumene, and part is produced by an efficient integration of phenol recovery from the aqueous waste streams from the phenol/acetone production process, e.g., hydroperoxide cleavage, and BPA production process, the overall process is improved economically and environmental friendly. The phenol recovered from the aqueous waste streams from, for example, the series of steps to separate and purify phenol and acetone in the crude product stream from the hydroperoxide cleavage step and from the BPA production step is purified and recycled for use in the reaction with acetone to reduce the overall consumption of phenol in the production of BPA.

Various procedures are taught for removing phenol from process waste streams. U.S. Pat. No. 3,963,610 describes a process for removing phenol from waste water that occurs in the manufacture of phenol by the cumene process using cumene as extractant. U.S. Pat. No. 6,071,409 similarly describes an extraction process using a tertiary amyl ether extractant to remove phenol. U.S. Pat. No. 5,344,528 describes a process for removing phenol by distillation from the waste water stream from a phenol plant with an objective of removing as much of the phenol as possible before sending the stream to a biological waste treatment facility. U.S. Pat. No. 6,824,687 describes a process suitable for phenol removal from waste water from a phenol/acetone plant.

European Pat. No. 0758636 B1 describes a two-step process for removing phenol and other educts and products from a BPA process waste water stream using a counter-current extraction process with an organic solvent followed by passing raffinate through an adsorption unit filled with polystyrene resin. U.S. Pat. No. 6,972,345 B2 describes a process for extracting phenol from waste water from a BPA process using a mixed solvent extractant of methyl isobutyl ketone, anisole and, optionally, mesitylene.

SUMMARY OF THE INVENTION

The present disclosure enables phenol recovery, purification and recycle in a simple, economic manner from waste water streams from, for example, a phenol/acetone production process, e.g., a phenol/acetone purification process step or an upstream cumene hydroperoxide cleavage process step, and from a BPA production step, for use in the reaction with acetone to produce BPA. The disclosure therefore reduces the overall consumption of phenol in the production of BPA.

Therefore, an aspect of the present disclosure involves an improved process for producing BPA comprising a step of reacting acetone with a stoichiometric excess of phenol under acidic conditions, possibly in the presence of a cocatalyst or promoter, to form a reaction product stream comprising crude BPA product wherein a portion of the phenol and, if desired, acetone, comprises phenol/acetone recovered from waste water streams generated by an upstream phenol/acetone production process, e.g., an upstream cumene hydroperoxide cleavage process step, and the BPA production process.

In another aspect, the present disclosure resides in an improved process for producing BPA comprising:

(a) recovering phenol and acetone from a crude product stream comprising phenol and acetone produced by a phenol/acetone production process, e.g., an upstream cumene hydroperoxide cleavage process step, which also produces an aqueous waste stream comprising water, unrecovered phenol and other reaction byproducts;

(b) reacting acetone with a stoichiometric excess of phenol, such as a portion of acetone form step (a) and phenol from step (a), in the presence of an acidic catalyst, possibly in the presence of a cocatalyst or promoter, such as a thiol compound, either homogeneously fed or heterogeneously bound to an acidic catalyst, to form a reaction product stream comprising crude BPA product, unreacted phenol, possibly unreacted acetone, possibly cocatalyst or promoter, water of condensation, and other reaction byproducts;

(c) distilling in single or multistage the reaction product stream from step (b) to distill off a first stream comprising water, a portion of unreacted phenol, possibly unreacted acetone, possibly cocatalyst or promoter or derivatives thereof if present in step (b), and other reaction byproducts, which constitutes the BPA waste stream, and a second stream having a portion of unreacted phenol; while sending downstream to a BPA purification step, the purification step comprising one or more solid-liquid separation and wash steps, the resulting concentrated BPA phenolic feed stream consisting essentially of phenol in which the BPA and byproducts have been concentrated;

(d) producing purified BPA by crystallization of the concentrated BPA phenolic feed stream of step (c); and (e) separating the purified BPA crystals of step (d) by solid-liquid separation, such as, for example, by centrifugation or filtration, and washing same in one or multiple stages with a wash stream which may include at least a portion of the second stream, or spent wash or mother liquor from subsequent crystallization, solid-liquid separation, and wash steps, to produce final washed BPA-phenol adduct, final spent wash and final mother liquor.

In some embodiments, the process of this disclosure comprises:

(f1) recovering phenol and possibly acetone from a BPA waste stream having the first stream by the steps of:
  (1) stripping any volatile sulfur compounds from the BPA waste stream;
  (2a) contacting the stripped BPA waste stream with an immiscible hydrocarbyl stream; wherein said immiscible hydrocarbyl stream comprises at least one of cumene, phenol, acetone, and alpha-methylstyrene (AMS): or
  (2b) after combining the stripped BPA waste stream with a phenol waste stream having a portion of the aqueous waste stream from step (a), contacting the combined stream with an immiscible hydrocarbyl stream to recover a portion of the phenol in the stripped BPA waste stream or the combined stream into the immiscible hydrocarbyl stream, wherein said immiscible hydrocarbyl stream comprises at least one of cumene, phenol, acetone, and alpha-methylstyrene (AMS); then
  (3) separating the phenol depleted stripped BPA waste stream, or the phenol depleted combined stream, as an aqueous stream from the immiscible hydrocarbyl stream; and
  (4) further recovering substantially all the phenol and acetone from the aqueous stream from step (3) by extraction, distillation, absorption, or a combination thereof, to produce an aqueous stream substantially free of phenol; or (f2) recovering phenol and possibly acetone from phenol/BPA waste stream(s) having the aqueous waste stream from step (a) and the first stream from step (c) by the steps of:
  (1) stripping any volatile sulfur compounds from the first stream from step (c);
  (2) combining the waste streams from steps (1) and (a) to form a combined waste stream; and
  (3) recovering substantially all the phenol and acetone from the combined waste stream from step (2) by extraction, distillation, absorption, or a combination thereof, to produce an aqueous stream substantially free of phenol; and (g) recovering and recycling the recovered phenol and/or acetone product of step (f1) or (f2) to steps (a) and/or (b).

In step (a) above, the recovered phenol and acetone may be from a phenol/acetone production process in which cumene hydroperoxide is reacted to form a crude product stream containing phenol, acetone, cumene, water, and other byproducts from the cleavage of cumene hydroperoxide, and in which a waste stream comprising water, unrecovered phenol, unrecovered acetone and other water-soluble byproducts from the cleavage of cumene hydroperoxide is also produced.

In step (f1) and step (f2) above, the BPA waste stream or the phenol/BPA waste stream may further comprise other waste streams comprising phenol and water derived from the BPA process in step (b) to step (e).

In step (f1) above, the aqueous stream in step (3) has less than 5 wt % phenol, preferably less than 2 wt % phenol.

The immiscible hydrocarbyl stream used in step (f1) and/or step (f2) may be obtained from any commercial process, preferably from a phenol/acetone production process, such as step (a), which comprises cumene, phenol, acetone, and alpha-methylstyrene (AMS). In one embodiment, the immiscible hydrocarbyl stream used in step (f1) is obtained from phenol/acetone production process of step (a). In another aspect, the present disclosure resides in an improved process for producing BPA comprising:

(1) contacting benzene and a $C_3$ alkylating agent, e.g., propylene, isopropanol or propyl chloride, under alkylation conditions with an alkylation catalyst in a reaction zone to produce an alkylation effluent comprising cumene;

(2) oxidizing the cumene from step (1) to produce the corresponding hydroperoxide;

(3) cleaving the hydroperoxide from step (2) to produce a crude product stream comprising phenol, acetone, water, unreacted cumene and other reaction byproducts, (4) processing the crude product stream from step (3) to recover phenol and acetone, and to produce a waste stream comprising water, unrecovered phenol, unrecovered acetone and other reaction byproducts;

(5) reacting acetone with a stoichiometric excess of phenol, such as a portion of the acetone from step (4) and phenol, such as from step (4), in the presence of an acidic catalyst, possibly in the presence of a cocatalyst or promoter, such as a thiol compound, either homogeneously fed or heterogeneously bound to an acidic catalyst, to form a reaction product stream comprising crude BPA product, unreacted phenol, possibly unreacted acetone, possibly cocatalyst or promoter, water of condensation, and other reaction byproducts;

(6) distilling in single or multistage the reaction product stream from step (5) to distill off a first stream comprising water, a portion of unreacted phenol, possibly unreacted acetone, possibly cocatalyst or promoter or derivatives thereof if present in step (5), and other reaction byproducts, which comprises at least a portion of the BPA waste stream, and a second stream having a portion of unreacted phenol; while sending downstream to a BPA purification step, the purification step comprising one or more solid-liquid separation and wash steps, the resulting concentrated BPA phenolic feed stream consisting essentially of phenol in which the BPA and byproducts have been concentrated;

(7) producing purified BPA by crystallization of the concentrated BPA phenolic feed stream of step (6); and (8) separating the purified BPA crystals of step (7) by solid-liquid separation, such as, for example, by centrifugation or filtration, and washing same in one or multiple stages with a wash stream which may include at least a portion of the second stream, or spent wash or mother liquor from subsequent crystallization, solid-liquid separation, and wash steps, to produce final washed BPA-phenol adduct, final spent wash and final mother liquor.

In some embodiments, the process of this disclosure further comprises:

(9a) recovering phenol and possibly acetone from a BPA waste stream having the first stream of step (6) by the steps of:
  (i) stripping any volatile sulfur compounds from the BPA waste stream,
  (ii) contacting the stripped BPA waste stream with an immiscible hydrocarbyl stream, or after combining the stripped BPA waste stream with a phenol waste stream having a portion of the aqueous waste stream from step (4), contacting the combined stream with an immiscible hydrocarbyl stream to recover a portion of the phenol in the stripped BPA waste stream or the combined stream from (i) into the immiscible hydrocarbyl stream, wherein the immiscible hydrocarbyl stream comprises at least one of cumene, phenol, acetone, and alpha-methylstyrene (AMS), then
  (iii) separating the phenol depleted stripped BPA waste stream, or the phenol depleted combined stream, as an aqueous stream from the immiscible hydrocarbyl stream; and
  (iv) further recovering substantially all the phenol and acetone from the aqueous stream from step (iii) by extraction, distillation, absorption, or a combination thereof, to produce an aqueous stream substantially free of phenol; or
(9b) recovering phenol and possibly acetone from phenol/BPA waste stream(s) having the waste stream from step (4) and the first stream from step (6) by the steps of:
  (i) stripping any volatile sulfur compounds from the first stream from step (6);
  (ii) combining the stripped first streams from steps (i) and waste stream from (4) to form a combined waste stream;
  (iii) recovering substantially all the phenol and acetone from the combined waste stream from step (ii) by extraction, distillation, absorption, or a combination thereof, to produce an aqueous stream substantially free of phenol; and
(10) recovering and feeding the recovered phenol and acetone product of step (9a) or (9b) to steps (4) and/or (5).

The immiscible hydrocarbyl stream used in step (9a)(ii) and/or step (9b)(ii) may be obtained from any commercial process, preferably from a phenol/acetone production process, such as step (4), which comprises cumene, phenol, acetone, and alpha-methylstyrene (AMS). In one embodiment, the immiscible hydrocarbyl stream used in step (9a)(ii) is obtained from phenol/acetone production process of step (4).

Conveniently, the $C_3$ alkylating agent in step (1) above comprises propylene or isopropanol.

The alkylation catalyst in step (1) above may comprise a molecular sieve selected from the group consisting of zeolite Beta, faujasite, mordenite, MCM-22, PSH-3, SSZ-25, ERB-1, ITQ-1, ITQ-2, ITQ-30, MCM-36, MCM-49, MCM-56 and mixtures thereof. Preferably, the molecular sieve is selected from the group consisting of MCM-22, PSH-3, SSZ-25, ERB-1, ITQ-1, ITQ-2, ITQ-30, MCM-36, MCM-49, MCM-56 and mixtures thereof.

In one embodiment, the contacting step (1) above is conducted under at least partial liquid phase conditions. Conveniently, the alkylation conditions include a temperature of up to about 250° C., a pressure up to about 250 atmospheres (25,000 kPa), a benzene to $C_3$ alkylating agent, e.g., propylene, molar ratio from about 0.5/1 to about 30/1 and a benzene weight hourly space velocity (WHSV) based on alkylating agent, e.g., propylene, from about 0.1 $hr^{-1}$ to about 250 $hr^{-1}$.

In one embodiment, the alkylation effluent produced in step (1) comprises polyisopropylbenzenes and the process further comprises contacting the polyisopropylbenzenes with benzene in the presence of a transalkylation catalyst to produce cumene. Conveniently, the transalkylation catalyst comprises a molecular sieve selected from the group consisting of zeolite Beta, faujasite, mordenite, USY, MCM-22, MCM-68, PSH-3, SSZ-25, ERB-1, ITQ-1, ITQ-2, ITQ-30, MCM-36, MCM-49, MCM-56 and mixtures thereof.

The oxidizing step (2) above may or may not be conducted in the presence of a catalyst, which catalyst can be a homogeneous catalyst or more preferably is a heterogeneous catalyst. Conveniently, the oxidizing step (2) is conducted at a temperature of from about 60° C. to about 200° C. and a pressure of from about 0 to about 1000 kPa.

Conveniently, the cleaving steps (a) and (3) above are conducted in the presence of an acidic catalyst, which can be a homogeneous catalyst or a heterogeneous catalyst. Cleaving steps (a) and (3) are conducted at a temperature of from about 20° C. to about 150° C., such as for example from about 40° C. to about 120° C., a pressure of from about 0 to about 7000 kPa, such as for example from about 100 to about 2860 kPa, and a liquid hourly space velocity (LHSV) based on the hydroperoxide of from about 0.1 to about 100 $hr^{-1}$, preferably from about 1 to about 50 $hr^{-1}$.

Suitable catalysts for steps (b) and (5) above include inorganic and organic acids, such as sulfuric acid and hydrogen chloride, and cationic exchange resins, optionally together with a cocatalyst or promoter, including a thiol promoter such as an alkyl mercaptan. As a non-limiting example, the condensation reaction of steps (b) and (5) may be conducted in the presence of added promoter, non-limiting examples of which include methyl mercaptan, ethyl mercaptan, 2,2-bis (methylthio) propane, and mercaptocarboxylic acid, e.g., mercaptopropionic acid. As further non-limiting examples, the condensation reaction of steps (b) and (5) may be conducted in the presence of added promoters comprising promoter-bound resins, including resins ionically-bound to quaternary amine groups contained in mercaptoalkylpyridines, or mercaptoalkylamines, the latter most often being 2-mercaptoethylamine derived from hydrolysis of 2,2 dimethylthiozolidine.

Conveniently, at least one of, and preferably each of, the contacting step (1), oxidizing step (2) and cleaving steps (a) and (3) may be effected by catalytic distillation.

In step (9a) and step (9b) above, the phenol/BPA waste stream(s) may further comprise other waste streams comprising phenol and water derived from the BPA process in step (5) to step (8.

In step (9a) above, the aqueous stream in step (iii) has less than 5 wt % phenol, preferably less than 2 wt % phenol.

DETAILED DESCRIPTION OF THE EMBODIMENTS

All patents, patent applications, test procedures, priority documents, articles, publications, manuals, and other documents cited herein are fully incorporated by reference to the extent such disclosure is not inconsistent with the present disclosure and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "volatile sulfur compound" or "volatile sulfur compounds" as used herein this disclosure means chemical compound(s) containing at least one atom of sulfur and, in its pure form, having a boiling point of less than 100° C., such as, less than 90° C., less than 80° C., less than 70° C., less than 50° C., less than 10° C., less than 5° C., less than 1° C., less than 0° C., at 101.3 kPa-a. The term 'volatile hydrocarbyl" or volatile hydrocarbyls" as used herein this disclosure means chemical compound(s) containing no sulfur atoms, at least one atom of carbon and, in its pure form, having a boiling point of less than 100° C., such as, less than 90° C., less than 80° C., less than 70° C., less than 50° C., less than 10° C., less than 5° C., less than 1° C., less than 0° C., at 101.3 kPa-a.

The present disclosure is directed to an improved, economical integrated process for producing BPA. One aspect of the process employs cumene as the source of the acetone and part of the phenol required to produce the BPA and employs a phenol recovery system to remove phenol from the waste streams of a phenol production process, e.g., a phenol/acetone plant or an upstream cumene hydroperoxide cleavage process step, and a BPA production process to produce an aqueous waste stream suitable for discharge to a biotreatment facility or direct discharge to the environment. The phenol removed and recovered from the waste streams is in sufficient purity for recycle to the phenol/acetone production process and/or acetone/phenol reaction process step to supplement the phenol needed for production of the BPA.

Alkylating benzene with a $C_3$ alkylating agent, such as propylene, produces cumene. The cumene is suitably purified by a fractionation method. The purified cumene is then oxidized to cumene hydroperoxide, which is subsequently decomposed to phenol and acetone.

Fractionation of the cleavage products produces phenol and acetone product streams, which can then be reacted to produce the desired BPA.

Cumene Production

The benzene employed in the alkylation step to produce cumene can be any commercially available benzene feed, but preferably the benzene has a purity level of at least 99 wt %.

The alkylating agent employed in the alkylation step to produce cumene can be any aliphatic or aromatic organic compound having one or more available alkylating aliphatic groups capable of reaction with benzene and having 3 carbon atoms. Examples of suitable $C_3$ alkylating agents include propylene; alcohols (inclusive of monoalcohols, dialcohols, trialcohols, etc.), such as n-propanol; aldehydes, such as propionaldehyde; and propyl halide, such as propyl chloride, with propylene being particularly preferred.

The alkylation catalyst employed in the alkylation step to produce cumene comprises a molecular sieve selected from the group consisting of zeolite Beta (described in U.S. Pat. No. 3,308,069), faujasite, mordenite, including dealuminized mordenite, members of the MCM-22 family of molecular sieves and mixtures thereof. Molecular sieves of the MCM-22 family include MCM-22 (described in U.S. Pat. No. 4,954, 325), PSH-3 (described in U.S. Pat. No. 4,439,409), SSZ-25 (described in U.S. Pat. No. 4,826,667), ERB-1 (described in European Pat. No. 0293032), ITQ-1 (described in U.S. Pat. No 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697). Preferred catalysts are members of the MCM-22 family.

The alkylation catalyst can include the molecular sieve in unbound or self-bound form or, alternatively, the molecular sieve can be combined in a conventional manner with an oxide binder, for example alumina, such that the final alkylation catalyst contains between about 2 and about 90 wt % molecular sieve.

The alkylation step is conducted such that the organic reactants, i.e., the benzene and $C_3$ alkylating agent, are brought into contact with the alkylation catalyst in a suitable reaction zone such as, for example, in a flow reactor containing a fixed bed of the catalyst composition or in a catalytic distillation reactor, under effective alkylation conditions. Such conditions include a temperature of up to about 250° C., e.g., up to about 150° C., e.g., from about 10° C. to about 125° C.; a pressure of about 250 atmospheres (25,000 kPa) or less, e.g., from about 1 to about 30 atmospheres (100 to 3,000 kPa); a benzene to alkylating agent, e.g., propylene, molar ratio from about 0.5/1 to about 30/1, e.g., about 1/1 to about 10/1; and a weight hourly space velocity (WHSV) based on alkylating agent of from about 0.1 $hr^{-1}$ to about 250 $hr^{-1}$, e.g., from about 1 $hr^{-1}$ to about 50 $hr^{-1}$.

The alkylation reactants can be in either the vapor phase or partially or completely in the liquid phase and can be neat, i.e. free from intentional admixture or dilution with other material, or they can be brought into contact with the alkylation catalyst composition with the aid of carrier gases or diluents such as, for example, hydrogen or nitrogen. Conveniently, the total feed to the alkylation step contains less than 1000 ppm, such as less than 500 ppm, for example less than 100 ppm, water. In addition, the total feed typically contains less than 100 ppm, such as less than 30 ppm, for example less than 3 ppm, sulfur, and less than 10 ppm, such as less than 1 ppm, for example less than 0.1 ppm, nitrogen.

Although the alkylation step is highly selective towards cumene, the effluent from the alkylation reaction will normally contain some polyalkylated products, e.g., polyalkylbenzene, as well as unreacted aromatic feed and the desired monoalkylated species. The unreacted aromatic feed is normally recovered by distillation and recycled to the alkylation reactor. The bottoms from this distillation are further distilled to separate the cumene product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically done in a transalkylation reactor, separate from the alkylation reactor, over a suitable transalkylation catalyst, such as an MCM-22 family catalyst, zeolite Omega, zeolite Beta, MCM-68 (see U.S. Pat. No. 6,014,018), zeolite Y, mordenite or a mixture thereof. The transalkylation reaction is typically conducted under at least partial liquid phase conditions. Suitable transalkylation conditions include a temperature of from about 50° C. to about 500° C., a pressure of from about 10 kPa to about 3,500 kPa, a weight hourly space velocity of from about 0.5 to about 500 $hr^{-1}$ on total feed, and benzene/polyalkylbenzene weight ratio of from about 0.1/1 to about 10/1.

Cumene Oxidation

The cumene product of the alkylation step described above is then oxidized to produce the corresponding hydroperoxide. The oxidation step is accomplished by introducing an oxygen-containing gas, such as air, into a liquid phase containing the cumene. The reaction can be performed in the absence of a catalyst, but the reaction rate can be improved by performing the oxidation in the presence of a catalyst, such as a water-soluble chelate compound in which multidentate ligands are coordinated to at least one metal selected from the group consisting of cobalt, nickel, manganese, copper, iron and mixtures thereof (See U.S. Pat. No. 4,013,725). A heterogeneous catalyst may be used. Suitable heterogeneous catalysts are described in U.S. Pat. No. 5,183,945, wherein the catalyst is an oxo (hydroxo) bridged tetranuclear manganese complex, and in U.S. Pat. No. 5,922,920, wherein the catalyst comprises an oxo (hydroxo) bridged tetranuclear metal complex having a mixed metal core, one metal of the core being a divalent metal selected from the group consisting of Zn, Cu, Fe, Co, Ni, Mn and mixtures thereof, and another metal being a trivalent metal selected from the group consisting of In, Fe, Mn, Ga, Al and mixtures thereof. The entire disclosures of the U.S. patents are incorporated herein by reference.

Other suitable catalysts for the oxidation step are the N-hydroxy substituted cyclic imides described in Published U.S. Patent Application No. 2003/0083527 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. These materials can be used either alone or in the presence of a free radical initiator and can be used as liquid phase, homogeneous catalysts or can be supported on a solid carrier to provide a heterogeneous catalyst.

Suitable conditions for cumene oxidation include a temperature from about 60° C. to about 200° C., such as from about 80° C. to about 120° C., and a pressure of from about 0 to about 1000 kPa.

A basic buffering agent may be added to the oxidation reaction to combine with acidic by-products that may form during the oxidation. In addition, an aqueous phase may be introduced, which can help dissolve basic compounds, such as sodium carbonate. The per-pass conversion in the oxidation step is preferably kept below about 50%, usually below about 30%, to minimize the formation of by-products. The hydroperoxides produced may be concentrated by distilling off the unreacted alkylbenzene prior to the cleavage step.

Hydroperoxide Cleavage

The cumene hydroperoxide produced in the oxidation step is subsequently cleaved to produce phenol and acetone, along with water and other reaction byproducts. The cleavage reaction is conveniently carried out in the presence of a catalyst in the liquid phase at a temperature of from about 20° C. to about 150° C., such as from about 40° C. to about 120° C., a pressure of from about 0 to about 7000 kPa, such as from about 100 to about 2860 kPa, and a liquid hourly space velocity (LHSV) based on the hydroperoxide of from about 0.1 to about 100 $hr^{-1}$, such as from about 1 to about 50 $hr^{-1}$. The hydroperoxide is preferably diluted in an organic solvent inert to the cleavage reaction, such as, for example, cumene, phenol or acetone, to assist in heat removal. The cleavage reaction is sometimes conducted in a catalytic distillation unit, in a reactor and heat exchanger circulation loop, or in a multi-stage reaction system.

The catalyst employed in the cleavage step can be a homogeneous catalyst or a heterogeneous catalyst.

Suitable homogeneous cumene cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

Suitable heterogeneous catalysts for use in the cleavage of cumene hydroperoxide include solid acid catalysts such as zeolite Beta, disclosed in U.S. Pat. No. 4,490,565; a Constraint Index 1-12 zeolite, such as ZSM-5, disclosed in U.S. Pat. No. 4,490,566; faujasite, disclosed in EP-A-492807; sulfonate-functionalized mesoporous crystalline materials known as M41S materials, e.g., MCM-41, disclosed in U.S. Pat. No. 6,441,251; smectite clays, described in U.S. Pat. No. 4,870,217; ion exchange resins having sulfonic acid functionality or heteropoly acids, such as 12-tungstophosphoric acid, on an inert support, such as silica, alumina, titania and/or zirconia, disclosed in U.S. Pat. No. 4,898,995. Additional solid acid catalysts suitable for use in the cleavage step include those comprising a sulfated transition metal oxide, such as sulfated zirconia, together with an oxide of iron or oxides of iron and manganese, as described in U.S. Pat. No. 6,169,216, as well as those comprising a mixed oxide of cerium and a Group IVB metal, e.g., zirconium, described in U.S. Pat. No. 6,297,406. The entire disclosure of each of the above patents is incorporated herein by reference.

The cumene hydroperoxide cleavage reaction can also be conducted in the presence of the solid acid catalyst disclosed in U.S. Pat. No. 6,169,215, incorporated herein by reference. Such a catalyst comprises an oxide of a Group IVB metal, such as zirconia or titania, modified with an oxyanion or oxide of a Group VIB metal, such as an oxyanion of chromium, molybdenum or tungsten, treated by calcination of the oxide species at a temperature of at least about 400° C., such as at least about 600° C., for example from about 700° C. to about 750° C. The modification of the Group IVB metal oxide with the oxyanion of the Group VIB metal imparts acid functionality to the material. The catalyst can also contain a metal selected from Groups IB, VIIB, or VIII of the Periodic Table, such as iron, manganese and/or copper.

Phenol/Acetone Production

The cleavage of cumene hydroperoxide produces an impure stream comprising phenol, acetone, cumene, water, alpha-methylstyrene (AMS) and other impurities from the upstream oxidation and cleavage steps. Additionally for homogeneously catalyzed cleavage of cumene hydroperoxide, this stream contains a catalytic concentration of acid. Phenol and acetone are separated and recovered from this stream through a purification process which also produces a waste stream comprising water, unrecovered phenol, unrecovered acetone and other reaction byproducts. This waste stream is the referenced waste stream from a phenol/acetone production process, such as the waste stream from steps (a) and (4) above.

BPA Production

The products of the cleavage reaction step are separated, conveniently by fractionation, into separate phenol and acetone streams. The phenol and at least part of the acetone can then be used for production of the desired BPA.

In general, BPA is produced in accordance with the above steps (b) through (e) or (5) through (8), by reacting acetone with a stoichiometric excess of phenol in the presence of an acidic catalyst, possibly in the presence of a cocatalyst or promoter, such as a thiol compound, either homogeneously fed or heterogeneously bound to an acidic catalyst, to form a reaction product stream comprising crude BPA product, unreacted phenol, possibly unreacted acetone, possibly catalyst, cocatalyst or promoter, water of condensation, and other reaction byproducts; (c) distilling in single or multistage the reaction product stream from step (b) to distill off a first stream comprising byproduct water from the condensation of phenol and acetone in step (b), a portion of unreacted phenol, possibly unreacted acetone, possibly cocatalyst or promoter or derivatives thereof if present in step (b), and other reaction byproducts, and a second stream having a portion of unreacted phenol, while sending downstream to a BPA purification step, the purification step comprising one or more solid-liquid separation and wash steps, the resulting concentrated BPA phenolic feed stream consisting essentially of phenol in which the BPA and byproducts have been concentrated; (d) producing purified BPA by crystallization of the concentrated BPA phenolic feed stream of step (c), where cooling for the crystallization is by any suitable means, including, if desired, vaporization of an alkane hydrocarbon or mixture of hydrocarbons containing from 4 to 6 carbons, e.g., pentane; (e) separating the purified BPA crystals of step (d) by solid-liquid separation, such as, for example, by centrifugation or filtration, and washing same in one or multiple stages with a wash stream which may include at least a portion of the second stream of volatilized unreacted phenol recovered from step (c), or spent wash or mother liquor from subsequent crystallization, solid-liquid separation, and wash steps, to produce final washed BPA-phenol adduct, final spent wash and final mother liquor; and (f1) recovering phenol and possibly acetone from the first stream in step (c) by the steps of (1) stripping any volatile sulfur compounds from the first stream; (2) contacting the stripped first stream from step (1) with an immiscible hydrocarbyl stream comprising at least one of cumene, phenol, acetone, and alpha-methylstyrene (AMS), or after combining the stripped first stream from step (1) with a portion of the aqueous waste stream from step (a), contacting the combined stream with an immiscible hydrocarbyl stream comprising at least one of cumene, phenol, acetone, and alpha-methylstyrene (AMS) to recover a portion of the phenol in the stripped first stream from step (1) or the combined stream into the immiscible hydrocarbyl stream; (3) separating the stripped first stream, or the combined stream, as an aqueous stream from the immiscible hydrocarbyl stream; and (4) further recovering substantially all the phenol and acetone from the aqueous stream from step (3) by extraction, distillation, absorption, or a combination thereof, to produce an aqueous stream substantially free of phenol; or (f2) recovering phenol and possibly acetone from the aqueous waste stream from step (a) and the first stream from step (c) by the steps of (1) stripping any volatile sulfur compounds from the first stream from step (c); (2) combining the waste streams from steps (1) and (a) to form a combined waste stream; and (3) recovering substantially all the phenol and acetone from the combined waste stream from step (2) by extraction, distillation, absorption, or a combination thereof, to produce an aqueous stream substantially free of phenol; and (g) recovering and recycling the recovered phenol and/or acetone product of step (f1) or (f2) to steps (a) and/or (b).The first stream of step (c) above, is the referenced waste stream from the BPA production step or more simply the BPA process waste stream. However, other waste streams comprising water and phenol derived from the BPA process steps (b) to (e) may be combined with the first stream of step (c) to form the BPA process waste water stream.

The term "recovering substantially all the phenol and acetone from stream(s)" as used herein means recovering at least 55%, 60%, 65%, 70%, 75%, 80%, 85%, 90%, or 95% by weight of the phenol and 55%, 60%, 65%, 70%, 75%, 80%, 85%, 90%, or 95% by weight of the acetone in the incoming stream(s). The term "aqueous stream substantially free of phenol" as used herein means that the aqueous stream has a phenol concentration of less than 100 ppmw, preferably less than 50 ppmw, and more preferably less than 10 ppmw. The term "substantially immiscible hydrocarbyl" as used herein means the fraction of hydrocarbyl present in the aqueous phase after contacting equal parts of hydrocarbyl with the incoming waste streams is less than 10%, 1%, or 0.1% by weight of the introduced hydrocarbyl stream.

As detailed herein, BPA is produced by the condensation reaction of excess phenol with acetone in the presence of an acid catalyst. Suitable catalysts for this reaction include inorganic acids, such as sulfuric acid and hydrogen chloride, and cationic exchange resins, optionally together with a cocatalyst or promoter, including a thiol promoter such as an alkyl mercaptan. Non-limiting examples of promoters include methyl mercaptan (MESH), ethyl mercaptan, 2,2-bis(methylthio)propane (BMTP), and mercaptocarboxylic acid, e.g., mercaptopropionic acid. As further non-limiting examples, the condensation reaction may be conducted in the presence of added promoters comprising promoter-bound resins, including resins ionically-bound to quaternary amine groups contained in mercaptoalkylpyridines, or mercaptoalkylamines, the latter most often being 2-mercaptoethylamine derived from hydrolysis of 2,2 dimethylthiozolidine.

More generally, the acid catalyst for step (a) is selected from the group consisting of homogeneous catalysts, heterogeneous catalysts and combinations thereof. The homogeneous acid catalyst is selected from the group consisting of inorganic acids. The heterogeneous acid catalyst is selected from the group consisting of ion exchange resins. The inorganic acid catalyst may be hydrochloric acid, sulfuric acid or a combination thereof. The heterogeneous acid catalyst may include an ion exchange resin made from sulfonated polymerized styrene monomer which has been cross linked with from about 1% to about 8% divinylbenzene (resin). Specific examples of suitable sulfonated resins are Amberlyst® 31, Lewatit® K-1221, Purolite® CT-124, Tulsion® 3845, and Dowex® 50WX4. The polymer may contain a promoter catalyst that is either ionically or covalently bonded to the polymer resin such as, for example, mercaptoethylamine. Alternatively, an unbound promoter catalyst such as, for example, methyl mercaptan (MESH), ethyl mercaptan or 2,2-bis(methylthiol)propane (BMTP) may also be fed to the reactor containing either a homogeneous or heterogeneous catalyst or combination thereof.

Suitable conditions for the condensation of phenol with acetone to produce BPA include an acetone/phenol molar ratio in the range of from about 1/30 to about 1/3, preferably from about 1/20 to about 1/4, a reaction temperature in the range of from about 40° C. to about 150° C., preferably from about 50° C. to about 100° C., and a weight hourly space velocity (WHSV) of from about 0.2 to about 30 $hr^{-1}$, preferably from about 0.5 to about 20 $hr^{-1}$. The BPA can then be separated from the condensation product as detailed above, e.g., by crystallization.

The waste stream from the BPA production step or the combined waste stream from the BPA production step and any phenol/acetone upstream process step is subjected to phenol recovery according to the present improved process disclosure to remove phenol from the waste stream of the BPA production step or combined waste streams from a phenol/acetone process and the BPA process to produce a final aqueous waste stream suitable for discharge to a biotreatment facility or direct discharge to the environment. The removed phenol is recovered in sufficient purity for recycle to the phenol/acetone upstream process step and/or the BPA production step.

The waste water from a BPA process step (c) using heterogeneous acid catalyst (for example, sulfonated acidic ion exchange resins) is an aqueous stream containing from about 5 to about 30 wt. % phenol with trace amounts of lower molecular weight hydrocarbyls such as acetone and methanol, and trace amounts of higher molecular weight hydrocarbyls such as isopropenyl phenol and p,p'-BPA. The BPA process step waste stream may be stripped to remove volatile sulfur compounds including co-fed promoters used in the condensation of phenol and acetone, their derivatives, and sulfur compounds evolved from ion-exchange resin catalyst with ionically bound thiol promoters. Examples of the volatile sulfur compounds include hydrogen sulfide, methyl mercaptan, ethyl mercaptan, and dimethyl or diethyl sulfide.

In a first embodiment of the present disclosure, the BPA production waste stream is first stripped to remove volatile sulfur compounds and then contacted, preferably first with an aqueous solution from the phenol/acetone production process containing from about 1 to about 25 wt. % of an alkali metal salt, for example, sodium sulfate, and then with the crude product stream from the hydroperoxide cleavage process containing sufficient cumene such that the ratio of phenol to cumene in the resulting immiscible hydrocarbyl phase is not greater than about 4:1, and preferably form about 2.5:1 to about 3.5:1. Hydrocarbyls in the BPA process step waste stream are then largely extracted into an immiscible hydrocarbyl phase that separates from the aqueous phase. The immiscible hydrocarbyl phase is subsequently fed to the phenol/acetone fractionation train where a series of distillation steps effectively separate trace hydrocarbyl compounds extracted from the BPA process step waste stream from the phenol and acetone product streams. Extracted higher molecular weight impurities, such as BPA, effectively exit the phenol process in the phenol residue stream.

At least a portion of the resulting aqueous phase containing unextracted phenol, phenate, and other unextracted hydrocarbyls, as well as any alkali metal salt, is transferred to a separate process for removal of the residual phenol and hydrocarbyls from the phenol waste stream. The method for removal of the phenol and other hydrocarbyls from the water phase may be one of any number of known processes employed for treating waste water from a phenol process based on decomposition of cumene hydroperoxide such as, but not limited to, extraction with an immiscible solvent, azeotropic distillation, or adsorption with activated carbon or polymeric adsorbents, or a combination thereof. The removed phenol and hydrocarbyls are then recovered and recycled within the phenol process. The specific method for recovery and recycle of the removed phenol depends on the method of removal employed. In this embodiment, no separate facility is required to recover phenol from the BPA waste water stream which improves the economic efficiency of the BPA production process.

Figure 1:
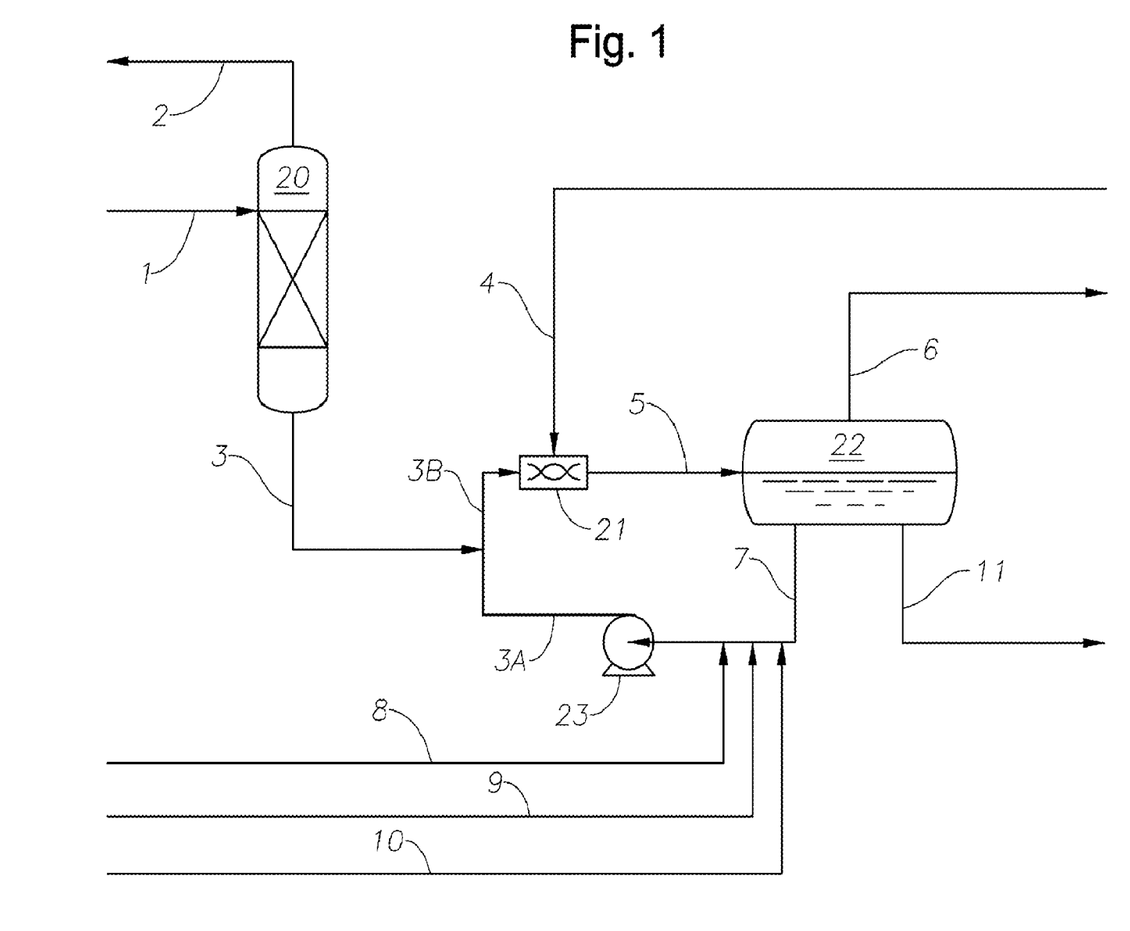
FIG. 1 depicts a phenol recovery system embodiment for use in the present disclosure.

Referring more specifically to the drawings, FIG. 1 shows a phenol recovery embodiment of the present disclosure. The BPA process step waste stream from, for example, step (6) or (c) via line 1 is fed to a stripping column 20 where volatile sulfur compounds may be separated and recycled to the BPA process step (5) or (b) via line 2. The stripped BPA process waste stream 3 is then mixed with an aqueous stream 3A containing alkali metal salt from recirculation pump 23. Optionally, the stripped BPA process water may be stored in a surge tank before it is mixed with the aqueous stream.

The combined aqueous stream 3B is fed to a contacting device 21 with a hydrocarbyl stream 4 comprising the crude product stream from cleavage of cumene hydroperoxide and sufficient cumene such that the ratio of phenol to cumene in the resulting immiscible hydrocarbyl phase is not greater than about 4:1 and preferably not greater than about 3.5:1. The purpose of the contacting device is to enhance the mass transfer of phenol from the aqueous phase into the hydrocarbyl phase. The mixed phases are fed to a settling vessel 22 via line 5, or alternatively to a decanting centrifuge, to separate the two liquid phases. The separated hydrocarbyl phase is transferred via line 6 to a downstream process to separate phenol, acetone and reaction byproducts. A portion of the separated aqueous phase is recirculated via line 7 by pump 23 to mix with the incoming stripped BPA waste water stream via line 3A. Process waste water from the phenol/acetone process step may be added to stream 7 via line 8 to recover valued hydrocarbyls. The pH of the separated aqueous phase in line 7 is controlled by the addition of a base stream such as, for example, sodium phenate, via line 9 or by addition of an acid such as, for example, sulfuric acid, via line 10 to the recirculated portion of the separated aqueous phase in line 7. Excess amounts of base, e.g., sodium phenate, may be added to recover the converted phenol into the separated hydrocarbyl phase. Phenol recovery is enhanced when the pH of the aqueous stream in line 7 is less than 7, preferably from about 5 to about 6. However, the aqueous stream may have pH greater than 7 if neutralization of organic or inorganic acids in the hydrocarbyl stream in line 4 is desired. In such case, the pH of the aqueous stream in line 7 is controlled from 7 to about 9, preferably from about 7.5 to about 8.5, to reduce phenate concentration in the stream.

The remaining portion of the separated aqueous phase is removed via line 11 and fed to a downstream dephenolation process employed for the phenol/acetone process waste water. The downstream dephenolation process removes the unextracted phenol and phenate present in that stream, typically from about 0.1 to about 2 wt. %, and from other waste water streams generated by the phenol/acetone process. The phenol concentration remaining in the water phase after passing through the downstream dephenolation process is less than about 100 ppm by weight, and preferably less than about 10 ppm. The water phase may be further treated to reduce its total organics content (TOC) by passing through a stripping column or an adsorption unit to remove soluble or entrained hydrocarbyls.

In a second embodiment of the disclosure, the BPA process step waste water stream from, for example, step (6) or (c), and the phenol process waste water stream from, for example, step (4) or (a), are combined into a single aqueous stream containing phenol from about 1 to about 20 wt. %, alkali metal salts from about 0 to about 10 wt. % and trace amounts of feedstock components and derivatives from both the BPA process and the phenol process. The embodiment may include stripping at least a portion of the BPA process waste water stream from step (6) or (c) to remove volatile sulfur compounds prior to its combination with the phenol process waste water stream, where at least a portion of the removed volatile sulfur compounds are recycled to the BPA process step. In such case, steam, nitrogen or other gas stream can be employed to remove volatile sulfur compounds such as mercaptans or sulfides from BPA process water stream.

The combined waste water stream is then fed to a single process for the purification of the waste water stream by removal of phenol and other hydrocarbyls and for the recovery of the removed phenol and other hydrocarbyls. The process for purification of the waste water stream may be one of any number of methods such as, but not limited to, extraction with an organic solvent, azeotropic distillation, or adsorption with activated carbon or polymeric adsorbents, or a combination thereof.

A preferred method for this phenol recovery embodiment is extraction of phenol and other valuable hydrocarbyls from the combined waste water stream using a water immiscible solvent. Phenol must preferentially distribute into the immiscible solvent. Useful extraction solvents include, but are not limited to, cumene, toluene, a mixture of cumene and alpha methyl styrene (AMS), ethers, such as methyl tert-butyl ether (MTBE), ethyl tert-amyl ether and diisopropyl ether, ketones, such as methyl ethyl ketone and methyl isobutyl ketone, and acetate esters, such as propyl acetate, butyl acetate, amyl acetate, and hexyl acetate.

Figure 2:
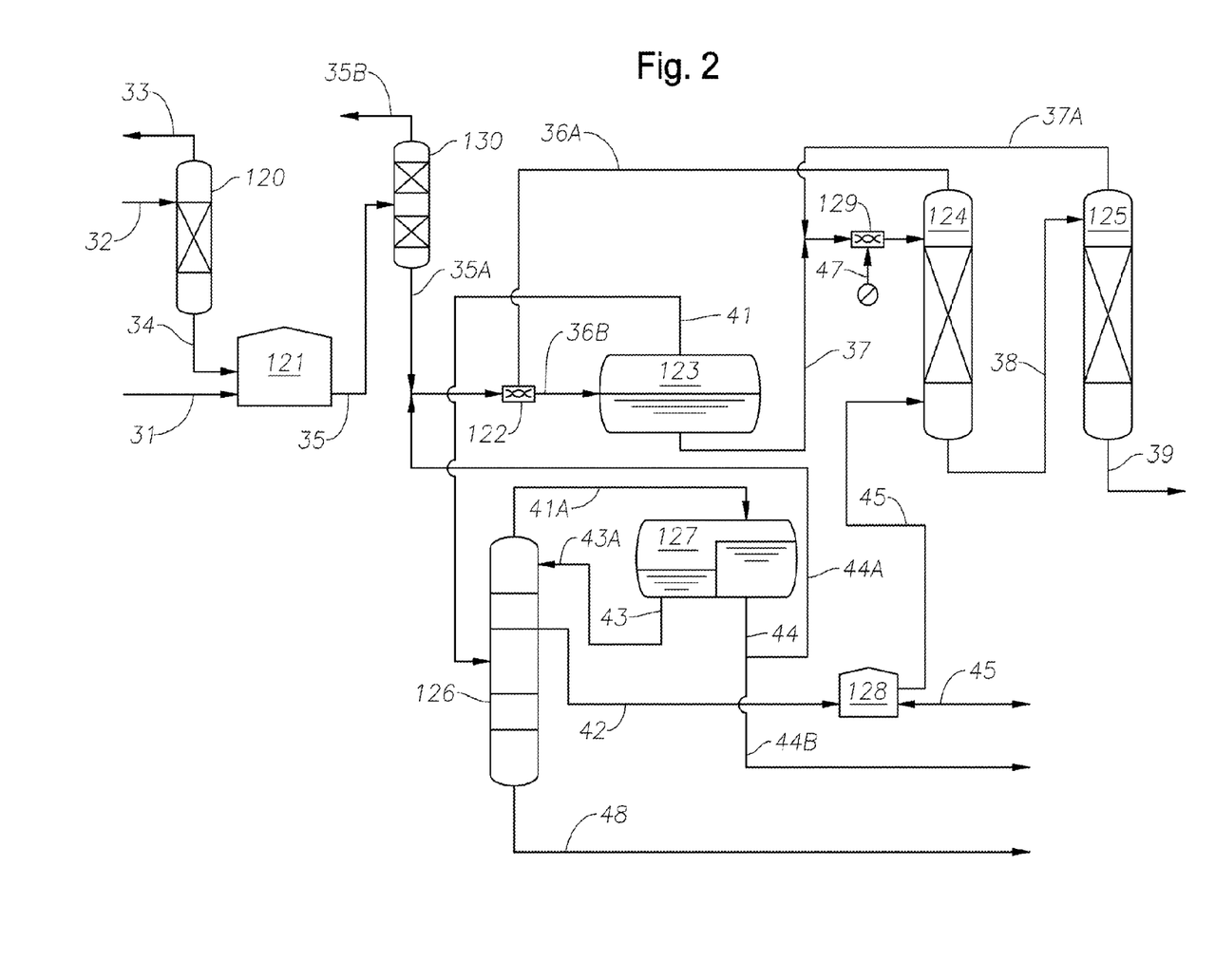
FIG. 2 depicts another phenol recovery system embodiment for use in the disclosure.

Again referring more particularly to the drawings, FIG. 2 shows a preferred process for this second embodiment. Volatile sulfur compounds are removed from the BPA process step waste water stream from, for example, step (6) or (c) via line 32 in a stripping column 120 before mixing with the phenol process waste water stream in line 31 via line 34. The combined waste water may optionally be stored in a surge tank 121 before feeding to the extraction process via line 35. The combined waste water in line 35 is preferably fed to a distillation column 130 where at least a portion of the acetone is removed overhead via line 35B and recycled to the phenol/acetone process to further purify the recovered acetone. The stream in line 35B is preferably introduced to the acetone fractionation train after acetone has been separated from the crude hydrocarbyl stream derived from the acid cleavage of cumene hydroperoxide, and before the separated acetone stream undergoes final purification. The bottoms stream from column 130 in line 35A and dilute extract via line 36A from the extraction column 124 are combined in a contacting device 122 designed to enhance the mass transfer of phenol to the organic phase. The mixed liquid phases are fed to a settling vessel 123 or a decanting centrifuge to separate the immiscible phases. The aqueous phase is subsequently fed via line 37 to the extraction column 124 with a plurality of theoretical stages to further reduce the phenol concentration. The aqueous phase is mixed with a strong acid such as, for example, sulfuric acid via line 47 in a contacting device 129 to control the extractor feed pH at from about 4 to about 7. Extractant solvent is fed to the extraction column 124 via line 46 and is dispersed into the continuous aqueous phase in a countercurrent flow pattern. The dispersed hydrocarbyl phase coalesces in the settling section of the extraction column 124. The dilute extract is then fed to the contacting device 122 as described above via line 36A. The resulting raffinate from the extraction column 124 in line 38 has phenol content less than about 100 ppmw, preferably less than about 10 ppmw. The raffinate pH is from about 5 to about 8, preferably from about 6 to about 7, to ensure efficient removal of phenol in the extraction column 124. The raffinate is then fed to a stripping column 125 via line 38 which removes soluble or entrained hydrocarbyls such as extractant solvent, to reduce total organic carbon (TOC) content of the effluent stream in line 39. Secondary treatment, such as biotreatment or polymer adsorption, may be additionally employed to further reduce TOC levels before discharge to the environment. The stripped hydrocarbyl vapors from the stripping column 125 via line 37A are condensed and combined with the aqueous feed in line 37 to the extraction column 124 via contacting device 129.

The concentrated extract phase from the settler 123 is fed via line 41 to a distillation column 126 in which the extraction solvent and extracted hydrocarbyls with lower normal boiling points than phenol are separated from the extracted phenol. The condensed overhead vapors are fed via line 41A to an accumulator 127 in which an immiscible water phase is formed and withdrawn via line 44. This stream contains water-soluble hydrocarbyls, such as, for example, acetone, acetol, formic acid and acetic acid. A portion of the withdrawn water phase is recycled via line 44A to surge tank 121, and another portion via line 44B is used to purge undesirable impurities such as, for example, formic acid, acetic acid and acetol from the process. The stream in line 44B is preferably routed to a downstream biotreatment facility, preferably in combination with the effluent stream in line 39.

The condensed hydrocarbyl phase in line 43 is decanted from the immiscible water phase in the accumulator 127 and at least a portion is returned via line 43 to the distillation column 126 as reflux. The extraction solvent is recovered as a separate side draw product from the distillation column 126 via line 42. The recovered extraction solvent in line 42 is then fed to a surge tank 128 and recycled via line 46 to the extractor 124. Fresh extraction solvent is added to the surge tank 128 via line 45 to maintain solvent inventory as needed.

The distillation column 126 bottoms stream in line 48 containing phenol and extracted hydrocarbyls with higher normal boiling points than phenol, such as bisphenols, is substantially free of the extraction solvent. The recovered phenol stream in line 48 is then fed to a phenol fractionation train to separate the undesirable trace organic compounds, such as from the more valuable hydrocarbyls such as phenol, cumene and AMS. The recovered phenol stream in line 48 is introduced to the phenol fractionation train, preferably after acetone has been separated from the crude hydrocarbyl stream derived from the acid cleavage of cumene hydroperoxide, and before phenol has been separated from hydrocarbyls with higher normal boiling points than phenol, such as, for example, cresols, acetophenone and AMS dimer. In this way, any extracted bisphenols are separated from the recovered phenol and purged from the process along with the above-mentioned compounds.

Alternately and for simplicity, both the recycled portion of the recovered hydrocarbyl in line 35B and the recovered phenol stream in line 48 may be introduced to the fractionation train before acetone has been separated from the crude hydrocarbyl stream derived from the acid cleavage of cumene hydroperoxide as the combined mass flows of these streams is substantially less than the mass flow of the crude hydrocarbyl stream derived from the acid cleavage of cumene hydroperoxide.

These and other facets of the present invention are exemplified by the following Examples.

Experimental Setup

BPA and phenol waste water were prepared according to the composition given in Table 1.

TABLE 1

Composition of BPA and phenol waste water streams

| | | Stream No. | |
|---|---|---|---|
| | | 1 | 2 |
| | | Stream Description | |
| Chemical | MW | Stripped BPA Waste Water wt % | Phenol Waste Water wt % |
| ACETONE | 58.08 | 0.8% | 1.2% |
| H$_2$O | 18.02 | 84.6% | 75.6% |
| PHENOL | 94.11 | 14.6% | 1.1% |
| ACETOL | 74.10 | — | 1.6% |
| Na$_2$SO$_4$ | 142.0 | — | 20.0% |
| Total | | 100.0% | 100.0% |

Cumene, butyl acetate (nBAc), diisopropyl ether (DIPE), tert-butyl methyl ether (MTBE) of ACS reagent grade or better were obtained from Aldrich Chemical as extraction solvents. A mixed solvent containing phenol, acetone, cumene and alpha-methylstyrene was also used. The experimental conditions are listed in Table 2.

TABLE 2

Experimental Conditions

| Comparative Example No. | Example Nos. | Extractant | Aqueous Feed/Extractant Weight Ratio | Extraction Temperature |
|---|---|---|---|---|
| 1 | 2, 3, 4 | N-Butyl Acetate (nBAc) | 6:1 | 30.0 |
| 5 | 6, 7, 8 | Diisopropyl Ether (DIPE) | 6:1 | 30.0 |
| 9 | 10, 11, 12 | MTBE | 6:1 | 30.0 |
| 13 | 14, 15, 16 | Cumene | 6:1 | 30.0 |
| 17 | 18, 19, 20 | Mixed Solvent * | 1:6 | 45.0 |
| — | 21, 22 | Mixed Solvent | 1:12 | 45.0 |

* Mixed solvent was made with 45 wt. % phenol, 35 wt. % acetone, 15 wt. % cumene, and 5 wt. % α-methylstyrene to form a mixture, which was subsequently saturated with water prior to its use.

The BPA waste water, phenol waste water, and an extraction solvent were charged into a 250-ml Erlenmeyer flask with glass cap. The content of the flask was vigorously mixed and subsequently placed in a shaker bath that maintained at 30° C. or 45° C. for at least twelve hours. The content of the flasks were again vigorously mixed prior to being transferred to a 125-ml glass separatory funnel for separation. Once the resulted two phases (organic and aqueous) became clear, they were separated to different sample containers for weight measurement and GC (FID/TCD) analysis. To accommodate the solubility limit, n-butanol was used as solvent for organic samples while water for aqueous samples during sample preparation.

COMPARATIVE EXAMPLES

For the comparative examples, the effectiveness of various extraction solvents for the recovery of phenol and acetone from the BPA waste water stream was measured. The distribution coefficient, D, and the recovery fraction, F, defined as follows were calculated to measure the effectiveness of the extraction, $$D = \frac{C_i^{Ch}}{C_i^{Aq}}$$

$$F = \frac{Q_i^{Fd} - Q_i^{Aq}}{Q_i^{Fd}} = 1 - \frac{Q_i^{Aq}}{Q_i^{Aq} + Q_i^{Ch} - Q_i^{Sol}}$$

where C and Q are the concentration and quantity of the component i, respectively. Fd and Sol denote the feed and solvent, respectively. Ch and Aq denote the organic and aqueous phase, respectively.

In cases where $Q_i^{Sol}=0$, the recovery fraction, F, is more simply expressed as $$F = \frac{Q_i^{Ch}}{Q_i^{Aq} + Q_i^{Ch}}$$

The BPA waste water and the extraction solvent were charged into a 250-ml Erlenmeyer flask with glass cap. The content of the flask was vigorously mixed and subsequently placed in a shaker bath that maintained at 30° C. or 45° C. for at least twelve hours. The content of the flasks were again vigorously mixed prior to being transferred to a 125-ml glass separatory funnel for separation. Once the resulted two phases (organic and aqueous) became clear, they were separated to different sample containers for weight measurement and GC (FID/TCD) analysis. The experimental results are shown for each solvent in Table 3 below:

TABLE 3

Comparative Example Results

| Comparative Example No. | Extractant | Aqueous Feed/Extractant Weight Ratio | Extraction Temperature | Phenol D | Phenol F | Acetone D | Acetone F |
|---|---|---|---|---|---|---|---|
| 1 | N-Butyl Acetate (nBAc) | 6:1 | 30.0 | 17.4 | 0.87 | 1.4 | 0.34 |
| 5 | Diisopropyl Ether (DIPE) | 6:1 | 30.0 | 14.9 | 0.84 | 1.2 | 0.30 |
| 9 | MTBE | 6:1 | 30.0 | 33.4 | 0.92 | 1.1 | 0.29 |
| 13 | Cumene | 6:1 | 30.0 | 7.3 | 0.70 | 2.8 | 0.47 |
| 17 | Mixed Solvent | 1:6 | 45.0 | 13.3 | 0.84 | 2.9 | −8.25 |

EXAMPLES

The illustrative examples employed the same extraction and analytical procedures as the comparative examples except that a portion of the phenol waste water was added to the BPA waste water before contacting with the extractant. The examples correspond to mixtures of 95% wt BPA waste water and 5% wt phenol waste water, 85% wt BPA waste water and 15% wt phenol waste water, and 50% wt BPA waste water and 50% wt phenol waste water.

Table 4 below shows the experimental results for each solvent for the mixed waste water streams. Distribution coefficients and recovery fractions for the experimental examples are improved relative to the corresponding comparative examples for all the tested solvents. Therefore, combining the phenol waste water with the BPA waste water improves the phenol and acetone recovery efficiency for a variety of solvent extraction processes.

The mixed solvent is substantially comprised of phenol and acetone with a relatively small amount of cumene and AMS. Surprisingly, the mixed solvent is still effective at recovering more than 80% of phenol from the BPA waste water. The negative values for the acetone recovery fraction indicate that a portion of the acetone in the solvent stream is transferred to the aqueous phase despite a distribution coefficient greater than 2. As with the other solvents, combining of the BPA and phenol waste water streams increases the phenol recovery fraction above 0.90 and retards the loss of acetone from the mixed solvent to the aqueous phase. This demonstrates another disclosed embodiment of contacting the BPA waste water stream with an immiscible hydrocarbyl stream of phenol, acetone, cumene and AMS of a composition similar to the effluent stream from the cleavage of cumene hydroperoxide in the phenol process.

TABLE 4

Demonstrative Example Results

| Example No. | Extractant | Aqueous Feed/ Extractant Weight Ratio | Extraction Temp | Phenol Waste Water wt % | Phenol | | Acetone | |
|---|---|---|---|---|---|---|---|---|
| | | | | | D | F | D | F |
| 2 | N-Butyl | 6:1 | 30.0 | 5 | 24.2 | 0.90 | 3.1 | 0.52 |
| 3 | Acetate | | | 15 | 31.9 | 0.91 | 4.0 | 0.57 |
| 4 | (nBAc) | | | 50 | 76.4 | 0.95 | 4.7 | 0.56 |
| 6 | Diisopropyl | 6:1 | 30.0 | 5 | 27.8 | 0.90 | 2.6 | 0.47 |
| 7 | Ether | | | 16 | 32.0 | 0.91 | 2.9 | 0.47 |
| 8 | (DIPE) | | | 50 | 64.8 | 0.94 | 4.1 | 0.51 |
| 10 | MTBE | 6:1 | 30.0 | 5 | 34.4 | 0.92 | 2.6 | 0.46 |
| 11 | | | | 15 | 44.9 | 0.93 | 2.8 | 0.47 |
| 12 | | | | 50 | 109.3 | 0.97 | 4.0 | 0.51 |
| 14 | Cumene | 6:1 | 30.0 | 5 | 7.5 | 0.69 | 8.4 | 0.71 |
| 15 | | | | 15 | 9.7 | 0.74 | 9.8 | 0.75 |
| 16 | | | | 51 | 16.6 | 0.81 | 12.7 | 0.76 |
| 18 | Mixed | 1:6 | 45.0 | 5 | 17.7 | 0.87 | 3.3 | −7.54 |
| 19 | Solvent | | | 16 | 23.2 | 0.90 | 4.2 | −5.14 |
| 20 | | | | 53 | 60.3 | 0.93 | 8.8 | −1.80 |
| 21 | Mixed | 1:12 | 45.0 | 16 | 26.0 | 0.93 | 4.6 | −3.04 |
| 22 | Solvent | | | 50 | 64.0 | 0.95 | 9.5 | −1.11 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A process for recovering phenol from a waste stream comprising water and phenol from a BPA production process, comprising the steps of:
   (A) contacting a first aqueous waste stream comprising water and phenol from a BPA production process and a crude phenol/acetone product stream comprising phenol, acetone, cumene, and alpha methyl styrene (AMS), produced by cleavage of cumene hydroperoxide in a phenol/acetone production process,
   (B) contacting the combined stream from step (A) with a second aqueous waste stream containing alkali metal salts, produced in a phenol/acetone production process,
   (C) separating the combined stream from step B to form an immiscible hydrocarbyl stream containing at least a majority of said phenol from said first aqueous waste stream and an immiscible second aqueous waste stream comprising less than 5 wt % of phenol; and
   (D) recovering substantially all the phenol from a portion of said immiscible second aqueous waste stream by extraction, distillation, absorption, or a combination thereof, to produce an aqueous stream substantially free of phenol from the phenol/acetone production process.

2. The process of claim 1, further comprising recycling at least a portion of said immiscible second waste stream from step (C) to combine with the first waste stream in step (A) before contacting the crude phenol/acetone product stream.

3. The process of claim 1, wherein said second aqueous waste stream comprises 0.5 wt % to 5 wt % phenol, 1 wt % to 20 wt % alkali metal salt, and at least 70 wt % water.

4. The process of claim 1, wherein said first waste stream comprises volatile sulfur compounds and said first waste stream is subjected to stripping prior to step (A).

5. The process of claim 1, wherein said first waste stream comprises at least 5 wt % phenol based on the total weight of said first waste stream.

6. The process of claim 1, wherein the process for producing BPA comprising the steps of:
   (A) reacting acetone with a stoichiometric excess of phenol in the presence of an acidic catalyst, possibly in the presence of a cocatalyst or promoter either homogeneously fed or heterogeneously bound to an acidic catalyst, to form a reaction product stream comprising crude BPA product, unreacted phenol, possibly unreacted acetone, possibly cocatalyst or promoter, water of condensation, and other reaction byproducts;
   (B) distilling in single or multistage the reaction product stream from step (A) to distill off a first stream comprising water, a portion of unreacted phenol, possibly unreacted acetone, possibly cocatalyst or promoter or derivatives thereof if present in step (A), and other reaction byproducts, which constitutes the BPA waste stream, and a second stream having a portion of unreacted phenol; while sending downstream to a BPA purification step, the purification step comprising one or more solid-liquid separation and wash steps, the resulting concentrated BPA phenolic feed stream consisting essentially of phenol in which the BPA and byproducts have been concentrated;

(C) producing purified BPA by crystallization of the concentrated BPA phenolic feed stream of step (B); and (D) separating the purified BPA crystals of step (C) by solid-liquid separation and washing same in one or multiple stages with a wash stream which may include at least a portion of the second stream, or spent wash or mother liquor from one or more subsequent crystallization, solid-liquid separation, and wash steps, to produce a washed BPA-phenol adduct, a spent wash stream and a mother liquor stream; and (E) heating and removing phenol from the washed purified BPA-phenol adduct from the final stage of crystallization and solid-liquid separation to produce a purified BPA melt stream where the removed phenol is recycled in whole or in part, to steps (A) or (C).

7. The process of claim 6, wherein step (A) is conducted in the presence of added promoter selected from the group consisting of methyl mercaptan, ethyl mercaptan, 2,2-bis(methylthio)propane, and mercaptocarboxylic acid.

8. The process of claim 1, wherein the upstream phenol/acetone production process comprises of a first process step to form cumene hydroperoxide by oxidation of cumene, a second process step to form phenol and acetone by cleavage of cumene hydroperoxide in the presence of an acid catalyst, a third process step to neutralize the effluent from the cleavage step, and a fourth process step to separate and purify the neutralized cleavage effluent to form purified phenol and acetone product streams.

\* \* \* \* \*